US010844794B2

(12) United States Patent
Prociw et al.

(10) Patent No.: US 10,844,794 B2
(45) Date of Patent: Nov. 24, 2020

(54) FUEL QUALITY MONITORING SYSTEMS

(71) Applicant: Delavan Inc, West Des Moines, IA (US)

(72) Inventors: Lev A. Prociw, Johnston, IA (US); Haralambos Cordatos, Colchester, CT (US)

(73) Assignee: DELAVAN INC., West Des Moines, IA (US)

( * ) Notice: Subject to any disclaimer, the term of this patent is extended or adjusted under 35 U.S.C. 154(b) by 732 days.

(21) Appl. No.: 15/387,150

(22) Filed: Dec. 21, 2016

(65) Prior Publication Data

US 2018/0171879 A1    Jun. 21, 2018

(51) Int. Cl.
| | | |
|---|---|---|
| *F02C 9/26* | (2006.01) | |
| *G01N 21/64* | (2006.01) | |
| *G01N 33/22* | (2006.01) | |
| *B64D 37/32* | (2006.01) | |
| *B64D 37/00* | (2006.01) | |
| *G01N 21/85* | (2006.01) | |

(52) U.S. Cl.
CPC ............... *F02C 9/26* (2013.01); *B64D 37/00* (2013.01); *B64D 37/32* (2013.01); *G01N 21/645* (2013.01); *G01N 21/85* (2013.01); *G01N 33/22* (2013.01); *G01N 2021/6417* (2013.01); *G01N 2021/6476* (2013.01); *G01N 2021/6478* (2013.01)

(58) Field of Classification Search
CPC ... G01N 2021/6417; G01N 2021/6476; G01N 2021/6478; G01N 21/645; G01N 33/22; B64D 37/00; F02C 9/26
See application file for complete search history.

(56) References Cited

U.S. PATENT DOCUMENTS

| | | | |
|---|---|---|---|
| 5,198,871 A | 3/1993 | Hill, Jr. et al. | |
| 5,490,387 A * | 2/1996 | Bisson | B64D 37/20 |
| | | | 137/586 |
| 6,184,973 B1* | 2/2001 | Baer | G01N 1/2813 |
| | | | 356/36 |
| 7,385,692 B1* | 6/2008 | Nguyen | G01J 3/02 |
| | | | 356/301 |
| 9,128,025 B2 | 9/2015 | Pastusiak et al. | |
| 2006/0263893 A1 | 11/2006 | Moses et al. | |
| 2008/0017758 A1 | 1/2008 | Johnson | |
| 2010/0165341 A1* | 7/2010 | Babico | G01N 15/1459 |
| | | | 356/336 |

(Continued)

FOREIGN PATENT DOCUMENTS

| | | |
|---|---|---|
| DE | 102012005058 A1 | 9/2013 |
| EP | 2778069 A1 | 9/2014 |
| JP | 2012168132 A | 9/2012 |

OTHER PUBLICATIONS

Specifications for PX2 Photometer—Photometric Analyzers; by Custom Sensors & Technology; revised on Mar. 2015.

(Continued)

*Primary Examiner* — Dominic J Bologna
(74) *Attorney, Agent, or Firm* — Locke Lord LLP; Daniel J. Fiorello; Scott D. Wofsy

(57) ABSTRACT

A fuel system includes a fuel line configured to allow a fuel to flow therethrough and a fluoroscopy device attached to the fuel line such that the fluoroscopy device can input excitation radiation into the fuel line and receive fluorescent radiation emitted from the fuel in the fuel line.

17 Claims, 1 Drawing Sheet

(56) References Cited

U.S. PATENT DOCUMENTS

| | | |
|---|---|---|
| 2010/0313591 A1 | 12/2010 | Lents et al. |
| 2014/0260626 A1* | 9/2014 | Kulczyk ................ B64D 37/32 |
| | | 73/592 |
| 2015/0051874 A1 | 2/2015 | Bommer et al. |
| 2015/0276627 A1 | 10/2015 | Clemen, Jr. |
| 2016/0313237 A1* | 10/2016 | Young ................... G01N 21/85 |
| 2016/0332743 A1 | 11/2016 | Teicholz et al. |
| 2017/0173275 A1* | 6/2017 | Anderson ............... A61M 5/46 |
| 2018/0299355 A1* | 10/2018 | Young ................ G01N 33/2858 |

OTHER PUBLICATIONS

M. Comodo, et al., presentation on Three-Dimensional Fluorescence Spectra of Thermally Stressed Commercial Jet A-1 Aviation Fuel in the Autoxidative Regime in Energy & Fuels; by ACS Publications.

Extended European Search Report, of the European Patent Office, dated Apr. 5, 2018, issued in corresponding European Patent Application No. 17208552.4.

\* cited by examiner

FUEL QUALITY MONITORING SYSTEMS

BACKGROUND

1. Field

The present disclosure relates to fuel quality monitoring systems (e.g., for aircraft fuel systems).

2. Description of Related Art

Fuel instability due to high temperature can lead to unwanted deposits in engine components during operation. Certain fuels are less stable at elevated temperatures due to higher concentration of contaminants which can deposit in a fuel distribution system, for example. High fuel temperatures are beneficial for improved specific fuel consumption and as an efficient heat sink for growing electrical and mechanical components on board aircraft, for example.

Fuel stability may improve with reduced oxygen content which may naturally occur at higher altitudes for a given length of time or with other effort to extract dissolved oxygen. When at altitude, oxygen can naturally degas from fuel. The fuel can be largely degassed and yet the original assumptions regarding acceptable upper temperatures are still used to limit temperature as a result of a lack of knowledge of actual oxygen content in the fuel, even though higher temperatures can be acceptable in view of the altitude dependent fuel qualities.

Such conventional methods and systems have generally been considered satisfactory for their intended purpose. However, there is still a need in the art for improved fuel quality monitoring systems. The present disclosure provides a solution for this need.

SUMMARY

A fuel system includes a fuel line configured to allow a fuel to flow therethrough and a fluoroscopy device attached to the fuel line such that the fluoroscopy device can input excitation radiation into the fuel line and receive fluorescent radiation emitted from the fuel in the fuel line. The fuel line can include a bend. The fluoroscopy device can be disposed at the bend.

The fluoroscopy device can be in line with a downstream portion of the fuel line at the bend. In certain embodiments, the bend can be a 90 degree turn, but any other suitable angle is contemplated herein.

The fluoroscopy device can include a laser source for providing the excitation radiation. Any other suitable excitation radiation source is contemplated herein. The fluoroscopy device can include a collecting lens disposed around the excitation radiation source for receiving fluorescent radiation from the fuel line around the excitation radiation source.

The collecting lens can be optically connected to a spectrometer circuit for analyzing the fluorescent radiation. In certain embodiments, the spectrometer circuit can be housed within the fluoroscopy device. The spectrometer circuit can include an intensity analyzer for determining fluorescent radiation intensity.

In accordance with at least one aspect of this disclosure, a fuel system includes a fuel line configured to allow a fuel to flow therethrough, a fluoroscopy device attached to the fuel line such that the fluoroscopy device can input excitation radiation into the fuel line and receive fluorescent radiation emitted from the fuel in the fuel line, a fuel heat exchanger configured to transfer heat from an aircraft system to the fuel, a bypass system for bypassing the fuel heat exchanger to prevent heat transfer from the fuel, and a controller configured to control the bypass system as a function of the fluorescent radiation received from the fuel in the fuel line.

The system can include a spectrometer circuit configured to receive the fluorescent radiation, wherein the controller can be operatively connected to a spectrometer circuit to control the bypass system based on signals from the spectrometer circuit as a function of the fluorescent radiation. The spectrometer circuit can include an intensity analyzer for determining an intensity of the fluorescent radiation, wherein the controller can control the bypass system as a function of the intensity of fluorescent radiation correlated to the input excitation radiation.

A method can include inputting excitation radiation into a fuel line, and receiving fluorescent radiation emitted from a fuel in the fuel line, and determining a quality of the fuel based on the fluorescent radiation. Inputting excitation radiation into the fuel line can include inputting excitation radiation at a bend in the fuel line.

Inputting excitation radiation into the fuel line can include inputting the radiation in line with a downstream portion of the fuel line at the bend. Inputting radiation can include using a laser source for providing the excitation radiation.

Receiving fluorescent radiation can include receiving the fluorescent radiation at a collecting lens disposed around the laser source for receiving fluorescent radiation from the fuel line around the laser source. Analyzing the fluorescent radiation can include utilizing an intensity analyzer for determining fluorescent radiation intensity.

Determining a quality of the fuel based on the fluorescent radiation can include analyzing the fluorescent radiation with a spectrometer. Determining a quality of the fuel can include determining at least one of a dissolved oxygen content of the fuel and a contamination levels of the fuel.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
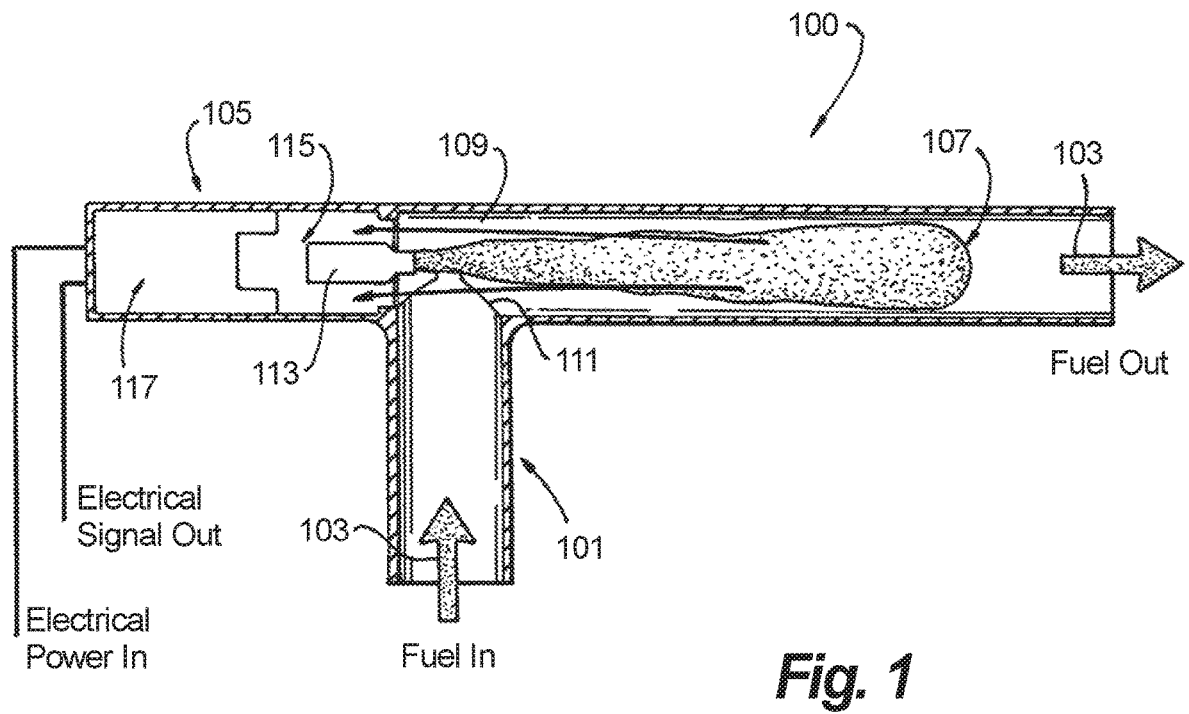
FIG. 1 is a schematic cross-sectional view of an embodiment of a fuel system in accordance with this disclosure.
Figure 2:
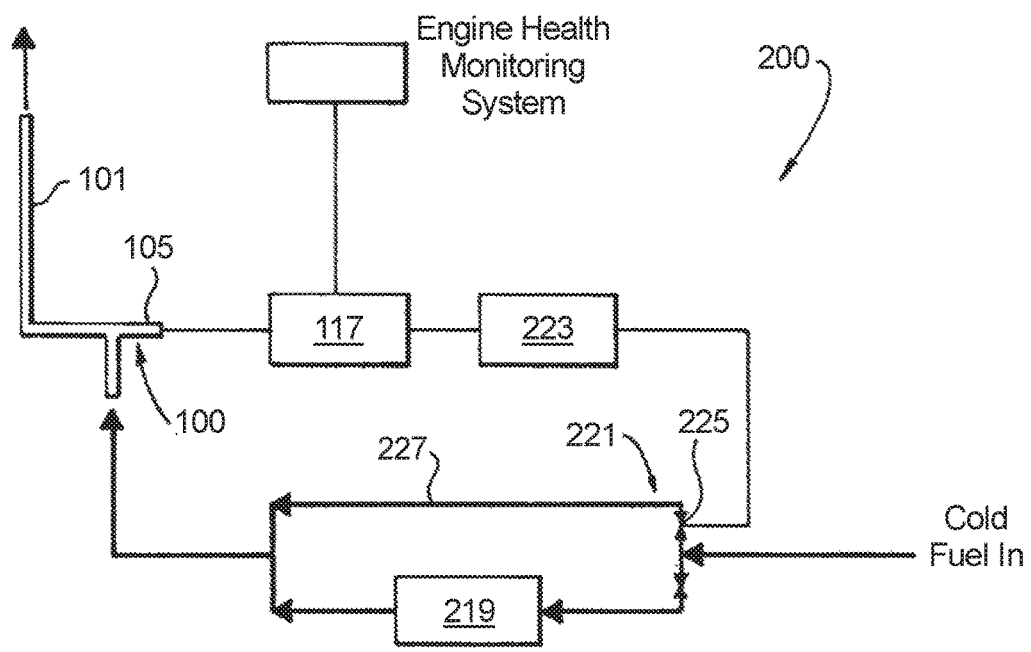
FIG. 2 is a schematic diagram of an embodiment of a fuel system in accordance with this disclosure.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIG. 2. The systems and methods described herein can be used to determine a fuel quality and/or modify heat transfer to a fuel in real time, for example.

Referring to FIG. 1, a fuel system 100 includes a fuel line 101 configured to allow a fuel 103 to flow therethrough. The system 100 includes a fluoroscopy device 105 attached to the fuel line 101 such that the fluoroscopy device 105 and input excitation radiation 107 into the fuel line 101 and receive emitted fluorescent radiation 109 from the fuel 103 in the fuel line 101.

The fuel line 101 can include a bend 111. In certain embodiments, as shown, the bend 111 can be a 90 degree turn, but any other suitable angle (or no angle) is contemplated herein.

The fluoroscopy device 105 can be disposed at the bend 111 or in any other suitable location. For example, the fluoroscopy device 105 can be disposed in line with a downstream portion of the fuel line 101 at the bend 111. In this regard, the excitation radiation 107 can be emitted in the same direction the fuel 103 is flowing in the fuel line 111. Such embodiments may have longer residence times in a suitable range of the fluoroscopy system 105.

Any other suitable configuration is contemplated herein. For example, the fluoroscopy system 105 can be configured as a t-fitting for retrofit onto existing fuel lines.

The fluoroscopy device 105 can include an excitation radiation source 113 for providing the excitation radiation 107. In certain embodiments, the excitation radiation source 113 can be a laser source (e.g., a laser diode configured for blue light). Any other suitable excitation radiation source is contemplated herein (e.g., a non-laser source such as an LED). The radiation source 113 can be configured to emit constant light, pulsing light, or any combination thereof.

The fluoroscopy device 105 can include a collecting lens 115 disposed around the excitation radiation source 113 for receiving fluorescent radiation 109 from the fuel line 101 around the excitation radiation source 113. It is contemplated that the lens 115 can be disposed separate from the radiation source 113 (e.g., in a different part of the fuel line 101) and/or can be arranged in any suitable manner related to the radiation source 113.

The collecting lens 115 can be optically connected to a spectrometer circuit 117 for analyzing the fluorescent radiation 109. In certain embodiments, the spectrometer circuit 117 can be housed within the fluoroscopy device 105 as shown. In certain embodiments, the spectrometer circuit 117 can include an intensity analyzer for determining fluorescent radiation intensity, for example. Any other suitable optical analysis systems and/or any suitable optical to electrical transducers are contemplated herein for signal creation, modification, and/or analysis of the fluorescent radiation 109.

In certain embodiments, a separate spectrometer can be utilized apart from the fluoroscopy device 105. Any suitable associated electronic circuits for analysis and/or communication are contemplated herein for use in and/or with the fluoroscopy device 105.

Referring to FIG. 2, a fuel system 200 includes any suitable embodiment of a system 100, e.g., as described above. The system 200 also includes a fuel heat exchanger 219 configured to transfer heat from an aircraft system (e.g., a fuel/oil cooler) to the fuel 103.

The system 200 also includes a bypass system 221 for bypassing the fuel heat exchanger 219 to prevent heat transfer from the fuel and a controller 223 configured to control the bypass system 221 as a function of the fluorescent radiation 109 received from the fuel 103 in the fuel line 101. The bypass system 221 can include a bypass valve 225 disposed on a bypass fuel line 227. The bypass valve 225 can be any suitable valve type to be controlled by the controller 223 and/or manually in any suitable manner.

The controller 223 can be operatively connected to a spectrometer circuit 117 to control the bypass system 221 based on signals from the spectrometer circuit 117 as a function of the fluorescent radiation 109. The controller 223 can be operatively connected to and control the bypass system 221 as a function of the intensity of fluorescent radiation 109 correlated to the input excitation radiation, for example.

The system 200 can include an engine health monitoring system that is operatively connected to the spectrometer circuit 117 to receive data therefrom to monitor and/or log engine health/coking, etc. In certain embodiments, the controller 223 can be integrated with the engine health monitoring system, a fuel controller, or any other suitable engine controller.

A method can include inputting excitation radiation into a fuel line, and receiving fluorescent radiation from a fuel in the fuel line, and determining a quality of the fuel based on the fluorescent radiation. Inputting excitation radiation into the fuel line can include inputting excitation radiation at a bend in the fuel line.

Inputting excitation radiation into the fuel line can include inputting the radiation in line with a downstream portion of the fuel line at the bend. Inputting radiation can include using a laser source for providing the excitation radiation.

Receiving fluorescent radiation can include receiving the fluorescent radiation at a collecting lens disposed around the laser source for receiving fluorescent radiation from the fuel line around the laser source. Determining a quality of the fuel based on the fluorescent radiation can include analyzing the fluorescent radiation with a spectrometer. Analyzing the fluorescent radiation can include utilizing an intensity analyzer for determining fluorescent radiation intensity.

Research has demonstrated "red shift" in fluorescence emission from stressed fuel samples indicative of a propensity to form coke. Fuel "stress" can be a function of temperature, contaminants, oxygen, etc., as appreciated by those having ordinary skill in the art. Embodiments allow measuring the intensity and/or wavelength of emitted fluorescence as a result of a certain excitation (e.g., at 450 nm when excited by 400 nm laser).

Embodiments can detect and determine periods of poor fuel stability during a mission. Fluorescence can be used to quantify the level of fuel stability or propensity to deposit carbon. Data of coking propensity (e.g., milligrams of coke formed per hour) can be created, e.g., during a mission using certain embodiments. Such data can be recorded and/or displayed (e.g., to pilot in flight).

If a poor fuel condition is determined, mitigating action (e.g., bypassing a heat source) can be taken. Prior technology used temperature as a fuel stability indicator. However when the oxygen level in the fuel is low (e.g., at high altitudes), temperature is a poor indicator of fuel stability. When the concentration of contaminants in the fuel is high, temperature is a poor indicator of fuel stability. Embodiments provide a way to accurately gauge fuel stability across varying regimes to allow a controller and/or user to decide on when sinking more heat to the fuel (e.g., for improving specific fuel consumption) is beneficial. Embodiments allow measurement of fuel qualities in real time to modify the allowed upper limit of fuel temperature.

While embodiments are described as fuel systems, it is contemplated that the term fuel system is to include any suitable fuel system or oil/lubrication system of an engine, and for any type of vehicle (e.g., aircraft, land vehicles).

The methods and systems of the present disclosure, as described above and shown in the drawings, provide for fuel systems with superior properties. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A fuel system, comprising:
a fuel line configured to allow a fuel to flow therethrough; and
a fluoroscopy device attached to the fuel line such that the fluoroscopy device can input excitation radiation into an interior of the fuel line, and not through a wall of the fuel line, and receive fluorescent radiation emitted from the fuel in the fuel line, wherein the fuel line includes a bend, wherein the fluoroscopy device is disposed at the bend.

2. The system of claim 1, wherein the fluoroscopy device is in line with a downstream portion of the fuel line at the bend.

3. The system of claim 2, wherein the bend is a 90 degree turn.

4. The system of claim 1, wherein the fluoroscopy device includes a laser source for providing the excitation radiation.

5. The system of claim 4, wherein the fluoroscopy device includes a collecting lens disposed around the laser source for receiving fluorescent radiation from the fuel line around the laser source.

6. The system of claim 5, wherein the collecting lens is optically connected to a spectrometer circuit for analyzing the fluorescent radiation.

7. The system of claim 6, wherein the spectrometer circuit is housed within the fluoroscopy device.

8. The system of claim 6, wherein the spectrometer circuit includes an intensity analyzer for determining fluorescent radiation intensity.

9. A method, comprising:
inputting excitation radiation into an interior of the fuel line and not through a wall of the fuel line;
receiving emitted fluorescent radiation from a fuel in the fuel line; and
determining a quality of the fuel based on the fluorescent radiation, wherein inputting excitation radiation into the fuel line includes inputting excitation radiation at a bend in the fuel line.

10. The method of claim 9, wherein the inputting excitation radiation into the fuel line includes inputting the radiation in line with a downstream portion of the fuel line at the bend.

11. The method of claim 10, wherein inputting radiation includes using a laser source for providing the excitation radiation.

12. The method of claim 11, wherein receiving fluorescent radiation includes receiving the fluorescent radiation at a collecting lens disposed around the laser source for receiving fluorescent radiation from the fuel line around the laser source.

13. The method of claim 9, wherein determining a quality of the fuel based on the fluorescent radiation includes analyzing the fluorescent radiation with a spectrometer.

14. The method of claim 13, wherein analyzing the fluorescent radiation includes an intensity analyzer for determining fluorescent radiation intensity.

15. The method of claim 9, wherein determining a quality of the fuel includes determining at least one of a dissolved oxygen content of the fuel and a contamination levels of the fuel.

16. A fuel system, comprising:
a fuel line configured to allow a fuel to flow therethrough; and
a fluoroscopy device attached to the fuel line such that the fluoroscopy device can input excitation radiation into an interior of the fuel line and receive fluorescent radiation emitted from the fuel in the fuel line,
wherein the fluoroscopy device includes:
a laser source for providing the excitation radiation; and
a collecting lens disposed around the laser source for receiving fluorescent radiation from the fuel line around the laser source.

17. A fuel system, comprising:
a fuel line configured to allow a fuel to flow therethrough; and
a fluoroscopy device attached to the fuel line such that the fluoroscopy device can input excitation radiation into the fuel line and receive fluorescent radiation emitted from the fuel in the fuel line, wherein the fuel line includes a bend, wherein the fluoroscopy device is disposed at the bend.

* * * * *